United States Patent
Faber et al.

(10) Patent No.: US 10,809,335 B2
(45) Date of Patent: Oct. 20, 2020

(54) CLOUD-BASED MR IMAGING

(71) Applicant: Siemens Healthcare GmbH, Erlangen (DE)

(72) Inventors: Roland Faber, Uttenreuth (DE); Marcus Wuebbe, Herzogenaurach (DE); Thomas Blum, Neunkirchen A. Br. (DE)

(73) Assignee: Siemens Healthcare GmbH, Erlangen (DE)

( * ) Notice: Subject to any disclaimer, the term of this patent is extended or adjusted under 35 U.S.C. 154(b) by 12 days.

(21) Appl. No.: 16/226,148

(22) Filed: Dec. 19, 2018

(65) Prior Publication Data

US 2019/0195976 A1 Jun. 27, 2019

(30) Foreign Application Priority Data

Dec. 22, 2017 (EP) .................................... 17210280

(51) Int. Cl.
| | | |
|---|---|---|
| *G01V 3/00* | (2006.01) | |
| *G01R 33/54* | (2006.01) | |
| *G16H 30/20* | (2018.01) | |
| *G01R 33/56* | (2006.01) | |
| *G06F 9/455* | (2018.01) | |

(52) U.S. Cl.
CPC ....... *G01R 33/543* (2013.01); *G01R 33/5608* (2013.01); *G06F 9/45533* (2013.01); *G16H 30/20* (2018.01)

(58) Field of Classification Search
CPC .............. G01R 33/543; G01R 33/5659; G01R 33/3415; G01R 33/36; A61B 5/055

USPC .................................................. 324/399, 309
See application file for complete search history.

(56) References Cited

U.S. PATENT DOCUMENTS

| | | | |
|---|---|---|---|
| 9,524,582 B2 | 12/2016 | Ma et al. | |
| 2013/0093829 A1* | 4/2013 | Rosenblatt | G09B 5/00 348/14.01 |
| 2013/0208955 A1 | 8/2013 | Zhao et al. | |
| 2014/0095868 A1* | 4/2014 | Korthny | G06F 21/64 713/165 |
| 2014/0278496 A1 | 9/2014 | Spencer | |
| 2015/0142462 A1* | 5/2015 | Vaidya | G06F 19/3418 705/2 |
| 2016/0239615 A1 | 8/2016 | Dorn | |
| 2016/0300016 A1 | 10/2016 | Dominick et al. | |
| 2017/0163569 A1* | 6/2017 | Koganti | H04L 49/25 |
| 2017/0206339 A1 | 7/2017 | Bertsch | |
| 2017/0293736 A1 | 10/2017 | Kramer et al. | |

* cited by examiner

Primary Examiner — Walter L Lindsay, Jr.
(74) Attorney, Agent, or Firm — Schiff Hardin LLP

(57) ABSTRACT

A magnetic resonance (MR) imaging system has an infrastructure within a cloud, designed to generate and/or activate and/or deactivate and/or terminate virtual systems on demand, which generate and operate multiple MR workflows as instances. The virtual systems has a cloud-based virtual MR host with an active MR workflow connected on demand to an MR control computer that operates an MR scanner to control an imaging process on the basis of one of the workflows. A client unit transmits patient-specific data to the virtual MR host and evaluates image data received from the virtual MR host.

11 Claims, 2 Drawing Sheets

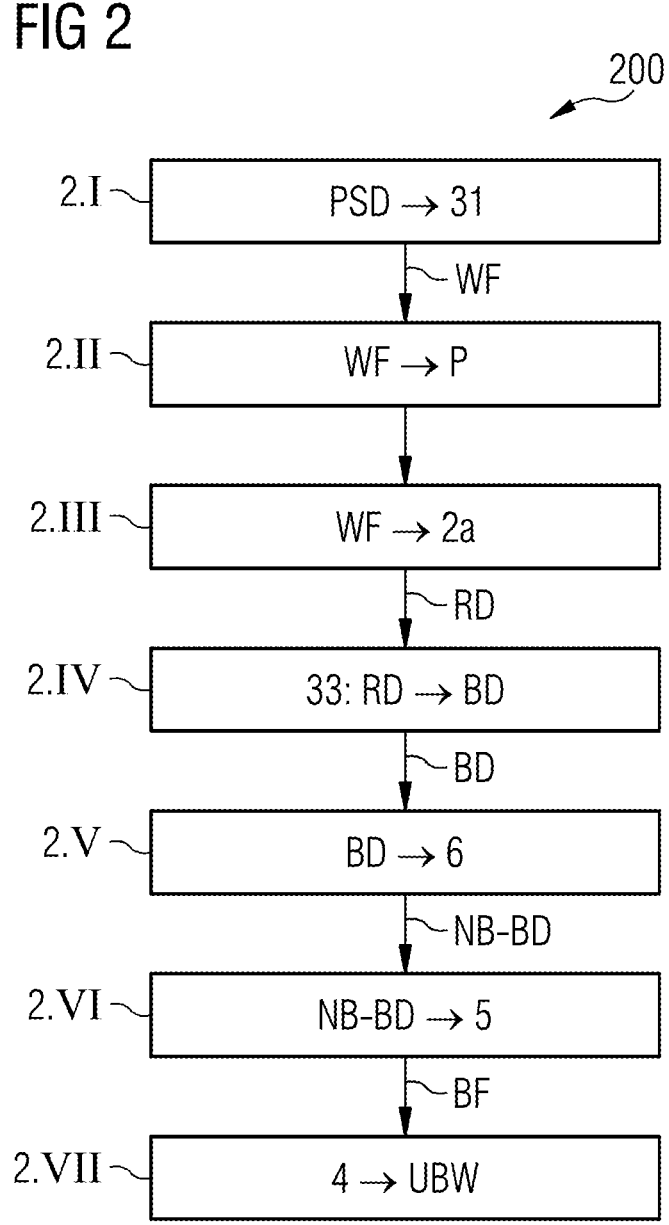

CLOUD-BASED MR IMAGING

BACKGROUND OF THE INVENTION

Field of the Invention

The invention concerns a magnetic resonance imaging system, and a method for carrying out a magnetic resonance imaging procedure.

Description of the Prior Art

In a magnetic resonance imaging system, also known as a magnetic resonance tomography system or magnetic resonance apparatus, in order to produce magnetic resonance recordings the body to be examined is exposed to a strong basic magnetic field, for example of 1.5, 3 or 7 tesla, with the use of a basic field magnet. In addition, a gradient magnetic field is applied by a gradient coil system. Using a radio-frequency (RF) transmit system radiates RF excitation signals by suitable antennas, in order to cause nuclear spins of particular atoms that are resonantly excited by this RF field to be tilted by a defined flip angle relative to the field lines of the basic magnetic field. When these nuclear spins relax, RF signals known as magnetic resonance (MR) signals are emitted, and are received by an RF receive system with suitable receiving antennas, and then further processed. From the raw data thereby acquired, the desired image data are reconstructed.

The computer resources used in a conventional magnetic resonance (MR) imaging system are not scalable, and therefore to some extent often remain unused or are sometimes not adequate in the case of a peak load. The computer resources installed in an MR system are conventionally defined on the basis of empirical values and are typically offered with resources so as to satisfy a maximum of each of two different options. The resources remain unused for most of the time and cause unnecessary installation costs. If a peak load is present, the user is forced to take unproductive remedial actions in order to provide the required resources.

If a new software system is to be implemented on the users' side, it may often take months until the software is ready for users to use. New MR system software is transmitted via an installation medium to the users, who arrange for a service technician to carry out an installation. The procedure often entails months of delays. Sometimes it takes years until new software is fully "rolled out" or introduced onto the market.

In order to use new MR system software, the users must often configure all processes for the new functionality of the software. In most cases there is no possibility of retaining adequate and well-established processes. If the new software still has shortcomings, the user can reactivate the old, tried-and-trusted software only by reinstallation on the MR system. Solutions tailored specifically to the user have to be migrated onto the new software in a complicated fashion, or are lost.

Large organizations require processes that are standardized centrally, which flexibly support distributed work, which has conventionally not been taken into account adequately in magnetic resonance imaging. For standardization purposes, workflows are manually copied at great cost in the case of users with multiple systems. In this case the chief technology director must have, for example, a USB stick brought to each MR system and the data entered there on site. Due to the significant amount of time required, adjustments to the standard are very costly.

As a very general overview, the publications United States Patent Application Publications 2016/0239615A1, 2016/0300016A1, 2017/0293736A1, and 2017/0206339A1 and U.S. Pat. No. 9,524,582 disclose the use of cloud technologies, particularly in connection with medical imaging devices.

Distributed working is supported, for instance, by the function Expert-i, which supports a type of remote control of an MR system in the form of a point-to-point connection. The remote client must be compatible with the MR system, which either requires unacceptable manual effort or customer-specific special solutions. Rescheduling patients on other MR systems is not supported, and diverting the workflow, i.e. the patient-specific workflow, to other work stations is possible only with the restriction that the user interface of the respective imaging system remains blocked.

SUMMARY OF THE INVENTION

Simplified maintenance and adjustment of MR systems in complex organization structures is therefore problematic, and it is an object of the present invention to address such problems.

The inventive magnetic resonance imaging system has an infrastructure within a cloud. The infrastructure generates and/or activates and/or deactivates and/or terminates virtual systems on demand. The infrastructure comprises resources, preferably an item of software or a computer program, with which the virtual systems are generated.

The virtual systems generate and operate a number of workflows as instances. In other words, the workflows are made available and carried out by the virtual systems via a communication network, for instance the Internet, in a hosting arrangement. A number of workflows can be operated by, in each case, one and the same set of virtual systems.

Each workflow contains information relating to the specific diagnostic problem for each affected patient, for example in the form of specific process details and parameter values for the measurement, as well as patient-specific information such as the height and weight or information relating to contrast agent tolerance.

Patient data such as information relating to diseases, allergies etc. influence the workflows. For instance, a patient with contrast agent allergy is subjected to a measuring method which differs from that of a patient who is contrast agent-tolerant. The selection of the workflows is primarily based on the diagnostic problem. The correct process is selected in a secondary step from the subset of processes suited to the problem in accordance with the patient's characteristics and is finally parameterized on a patient-specific basis, for example in order to take into account the precise position of an organ or the specific absorption rate in accordance with the weight of the patient.

The infrastructure preferably enables a generation and an activation and a deactivation as well as a termination of the virtual systems. Virtual systems are advantageously generated on demand and can be modified or replaced or deleted as active systems depending on the application, so that hardware resources are protected and the data load of the magnetic resonance imaging system can be reduced. The virtual systems include at least one cloud-based virtual MR host with an active MR workflow which is connected on demand to the MR control computer. A virtual MR host is to be understood as a virtual host computer, which stores and processes a workflow of an MR imaging process, and carries it out and makes it available to the operation of the MR system. A cloud-based, virtual MR host is to be understood as an MR host, the function of which is made available, for instance with the aid of a computer program installed in the cloud, via a computer network, for instance the Internet, without a local host computer having to be provided and without a corresponding computer program having to be installed on local computers for the purpose of generating and activating MR workflows.

Furthermore, the magnetic resonance imaging system has an MR scanner with an MR control computer. The MR control computer is designed to control an imaging process of the MR scanner on the basis of one of the workflows stored in the virtual MR host. Because parts of the control of the magnetic resonance imaging system are in virtual form, the inventive magnetic resonance imaging system can also have a number of MR scanners, which are all activated by the virtual MR host.

Moreover, the magnetic resonance imaging system has at least one client processor for transmitting patient-specific data to the virtual MR host and for evaluating image data received from the virtual MR host.

The computer resources available in the cloud may advantageously be used on demand by an activated MR workflow. Instead of acquiring a host computer for each individual system, these resources can be moved into the cloud, and agreements known as pay-per-use contracts with local cloud providers can be established for their use. The redundancy of computer resources for local solutions is avoided. The user must only pay for those resources that the user actually uses. Manual unproductive remedial work for the purpose of releasing required resources at inconvenient points in time, for instance when a patient is already on the bed in the MR scanner, is no longer necessary. A number of MR scanners can advantageously be activated by one client with the use of the virtual MR host, so that, if necessary, a more comprehensive imaging of a patient is possible, without primary data having to be entered repeatedly.

In large medical facilities, server systems in the form of private clouds can be set up, which flexibly scale workflow-specific resources for peak loads.

New software can be provided in the cloud at any time. As soon as the software is available in the cloud, the user can start an MR workflow with the new software at any time. The distribution of new software versions is therefore simplified and accelerated. A lengthy "roll-out" of the software onto the market is no longer necessary.

Furthermore, when the software on the virtual MR host is renewed, there is no obligation to eliminate the old software since both program versions can be available in parallel in the cloud. The user thus can decide whether the user would like to access the new software version for a workflow or whether he would prefer to use the tried-and-trusted old program version with well-established processes. Should the new software still have shortcomings, the user can use the old, tried-and-trusted software at any time, without having to carry out a reinstallation. The user is also not obliged to train his entire personnel for a new item of software: specific specialists can use the new functionality while others still continue to use the tried-and-trusted procedures. User-specific solutions can be migrated independently on demand, since they remain available to the user in the older variant.

Moreover, a standardization of a workflow to be used is enabled, particularly in the case of use by major customers. To this end the user applies an MR reference workflow in the cloud. This reference workflow can be used immediately by all work stations or clients connected to the cloud. Changes to the reference workflow are firstly carried out centrally in the cloud and are then available immediately.

Active instances of a workflow can be relayed from client to client, wherein all previous results are available immediately for further processing without a loading process. Active instances of workflows are to be understood as loaded and active programs in the system, which carry out these workflows. In the case of interruptions and for the purpose of long-term documentation, workflow instances can be stored in the cloud. These stored instances can be reactivated on demand. Major users in particular are supported optimally by the cloud technology. Following the introduction of 5G broadband communication, collaboration for the purpose of diagnosing the state of health of a patient is even possible on a worldwide basis. Furthermore, the data stored in the cloud can be used for data mining.

With the inventive method for carrying out a magnetic resonance imaging procedure, patient-specific data is transmitted from a client unit to at least one cloud-based virtual MR host, which executes one active MR workflow from a plurality of stored MR workflows in the cloud. Furthermore, the virtual MR host is connected to a suitable MR scanner by way of an MR control computer connected to the MR scanner for a subsequent communication. A suitable MR scanner is an MR scanner that is adapted to the patient-specific workflow. The active, patient-specific workflow is then transmitted from the virtual MR host to the MR control computer of the MR scanner. On the basis of the patient-specific active workflow, the MR scanner is then activated by the MR control computer. The raw data generated by the MR scanner in the imaging process are further transmitted to the virtual MR host. The MR host can then provide functionalities for further processing the raw data, such as for reconstructing image data. The image data generated are relayed to at least one client processor. Image data received from the virtual MR host are evaluated by the at least one client processor. The inventive method shares the advantages of the inventive magnetic resonance imaging system.

After the addition of corresponding hardware, such as suitable server capacities and data transmission capacities in the cloud, some components of the inventive magnetic resonance imaging system can be embodied predominantly in the form of software components. This relates in particular to parts of the cloud-based MR host and the client units.

A largely software-based realization has the advantage that computer systems currently already available for data transmission between individual components of magnetic resonance imaging systems can also be used easily by a computer program installed in the cloud in order to work in the manner according to the invention. In this respect the above object is also achieved in accordance with the invention by a non-transitory, computer-readable storage medium encoded with a program code, which can be loaded directly into a memory of a computer of a cloud or cloud-based server system. The program code cause the computer to carry out all the steps of the method according to the invention, when the program code is executed by the computer of the magnetic resonance imaging system.

A computer program product can include, apart from the basic program code, additional components, if relevant, such as documentation and/or additional components including hardware components such as hardware keys (dongles, etc.) in order to use the software.

In an embodiment of the inventive magnetic resonance imaging system, the virtual systems have a cloud-based virtual image reconstruction device, which is designed to receive raw data from the MR scanner and reconstruct image data on the basis of that raw data.

The reconstruction advantageously proceeds in a centralized manner. Any adjustments to specific requirements or any updates need only take place once. The modified software can then be used to reconstruct raw data from various MR scanners.

In another embodiment of the inventive magnetic resonance imaging system, the virtual systems have a virtual host controller, which is designed to control the access of client units to the virtual MR host. Such a virtual host controller can prevent unauthorized access to the MR host, for instance, so that the general security and data security of the MR system are improved.

In another embodiment of the inventive magnetic resonance imaging system, the at least one client processor has at least one of the following client types:
- a scan connection client,
- a post-processing client,
- a rendering client and
- a referring client.

The scan connection client allows access to an MR system or the operation of an MR system by a user. In the simplest case, the scan connection client is used as a virtual control console of the MR scanner.

A post-processing client is used to process the reconstructed image data. For instance, this post-processing can be the processing of grayscale values, filter operations and folds as well as the selection of suitable image displays for the diagnosis.

The rendering client is used to carry out diagnosis operations. Suitably post-processed images of an examination area of a patient are shown visually to a radiologist on the monitor of the rendering client.

The radiologist can make a diagnosis on the basis of the visual images.

A referring client is used to refer a patient to suitable specialist facilities on the basis of a diagnosis result. The clients occupied with different tasks can advantageously access all the data stored centrally in the cloud, so that no unnecessary redundancy exists or no repeatedly generated and possibly differing data can be used by the individual clients.

BRIEF DESCRIPTION OF THE DRAWINGS

FIG. 2 is a flowchart that illustrates the method for carrying out a magnetic resonance imaging procedure according to an exemplary embodiment of the invention.

DESCRIPTION OF THE PREFERRED EMBODIMENTS

Figure 1:
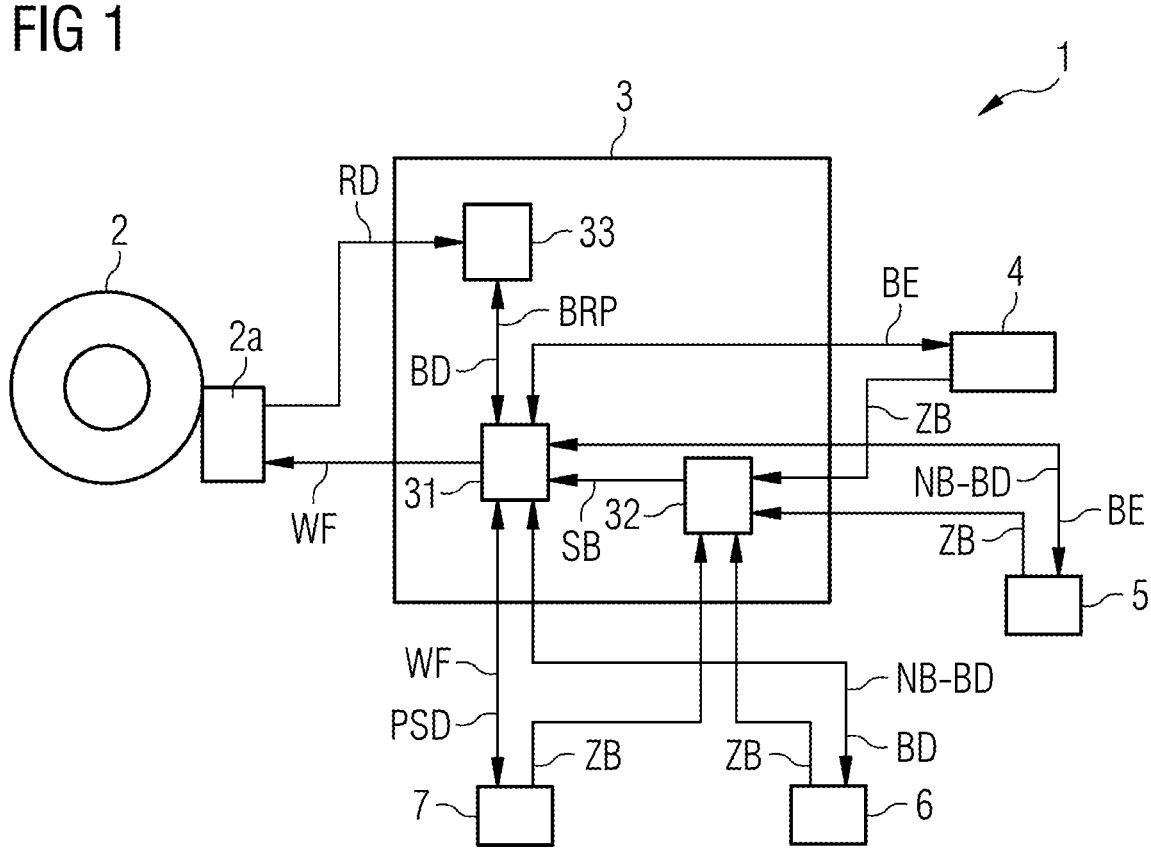
FIG. 1 is a block diagram that illustrates a magnetic resonance imaging system according to an exemplary embodiment of the invention.

A magnetic resonance imaging system 1 according to an exemplary embodiment of the invention is shown schematically in FIG. 1. The magnetic resonance imaging system 1 has an MR scanner 2, which is operated by an MR control computer 2a. For carrying out an imaging procedure on a specific patient, the MR control computer 2a obtains a flow chart referred to as a workflow (WF), which has information, measuring programs and instructions tailored to the specific use case. Workflows WF for different use cases are stored centrally in a cloud 3 and are activated on demand in the form of a virtual MR host computer 31, which is connected to the MR scanner 2 on demand. Patient-specific data PSD is entered with the aid of a scan connection client 7 for the selection and configuration of the MR workflow WF. Only one scanner 2 is shown in FIG. 1, but the virtual MR host 31 can also be connected to multiple, different MR scanners. In an MR imaging process of a patient, raw data RD are generated by the MR scanner 2 and are provided to the MR control computer 2a, and from there are transmitted to a virtual image reconstruction processor 33 disposed in the cloud 3 or generated in the cloud 3. The virtual image reconstruction device 33 reconstructs image data BD on the basis of the obtained raw data RD. A reconstruction program BRP that may be tailored to the specific use case obtains the virtual reconstruction device 33 from the virtual MR host 31. The generated image data BD are transmitted from the virtual image reconstruction processor 33 to the MR host 31. The virtual MR host 31 stores the image data BD centrally in the cloud 3 and transmits the image data BD to different client processors 4, 5, 6, 7. The individual client processors 4, 5, 6, 7 obtain access to the virtual MR host 31 via a virtual host controller 32, which regulates and monitors the access of the client processors 4, 5, 6, 7 to the virtual MR host 31 and may enable access to the virtual MR host 31 with control commands SB.

The scan connection client 7, also referred to as the technologist's control console, is used to display the workflows on the monitor and for primary inputs. Primary inputs comprise patient information and specific values of examination and image calculation parameters.

Within the scope of an imaging procedure, a measurement preparation is firstly carried out by way of the aforementioned scan connection client 7, wherein a suitable workflow WF is generated in the form of the aforementioned virtual systems 31, 32, 33 and is adjusted accordingly. In the course of the rest of the imaging process, the actual image acquisition of a patient, which includes an acquisition of raw data RD by means of the scanner 2 and a reconstruction of image data BD in the virtual image reconstruction processor 33, is now carried out under the control of the MR control computer 2a and while applying the generated workflow WF. The reconstructed image data BD are then retrieved from the virtual MR host 31 by a post-processing client 6, which is used to post-process the image data BD. To this end an access request ZB is again first directed to the host controller 32, which grants access to the virtual MR host 31 after checking the access requirements, in order to read out the reconstructed image data BD from there. The post-processed image data NB-BD are then stored again in the virtual MR host 31, in order to be available for subsequent evaluation steps. A reporting client 5 is used to carry out a diagnosis on the basis of any post-processed image data NB-BD. To this end, an access request ZB is again directed to the host controller 32, which grants access to the virtual MR host 31 in order to read out reconstructed image data NB-BD from there. The post-processed image data NB-BD are then shown on a monitor of the reporting client 5 and used for diagnosis purposes. The diagnosis result BE is again transmitted back to the virtual MR host 31 and is stored there. If a referral is necessary, this is carried out with the use of the referring client 4, which depends on the diagnosis results BE stored in the MR host 31.

FIG. 2 shows a flowchart 200 that illustrates a method for carrying out a magnetic resonance imaging procedure. In step 2.I, patient-specific data PSD is transmitted from a scan connection client 7 to a cloud-based virtual MR host 31, which comprises a plurality of MR workflows, and a suitable workflow WF may also be selected in the virtual MR host 31. The workflow WF is activated for instance while taking into account the relevant patient P's medical history, such as available images of a prior examination, lab results, intolerances etc. In step 2.II, the prepared workflow WF is then taken over by a specialist for the MR system used and assigned permanently to the MR system and the patient P. If considered necessary, the specialist can also tailor the workflow WF for, and allocate it to, another MR system. Subsequently in step 2.III, the patient-specific workflow WF is transmitted from the virtual MR host 31 to an MR control computer 2a of a selected MR scanner 2. In step 2.III, the MR scanner 2 is also controlled by the MR control computer 2a on the basis of the patient-specific workflow WF such that raw data RD about the patient are acquired and transmitted to a cloud-based image reconstruction device 33. In step 2.IV, image data BD is reconstructed by the image reconstruction device 33 on the basis of the raw data RD. The image data BD are transmitted in step 3.V below from the cloud 3 to a post-processing unit, also known as a post-processing client 6. The visual representations, also called hangings, which are optimal for a diagnosis are prepared by a specially trained technologist, and supplemented by automatic routine post-processing so that post-processed image data NB-BD are produced. In step 3.VI the post-processed image data NB-BD is then transmitted to a reporting client 5 and examined there by a radiologist, who then produces a diagnosis BF. In step 3.VII, a referral UBW is finally produced by a referring client 4 in accordance with the determined diagnosis BF.

It should again be noted that the methods and devices described above are preferred exemplary embodiments of the invention, and the invention can also be varied by those skilled in the art without departing from the scope of the invention. For completeness, it should be noted that the expression "unit" does not preclude this entity from being formed by a number of components, which may be spatially distributed.

The invention claimed is:

1. A magnetic resonance (MR) imaging apparatus, comprising:
    an infrastructure within a cloud configured to apply an action on demand to virtual systems that generate and operate a plurality of MR workflows as instances, the action including at least one of generating the virtual systems, activating the virtual systems, deactivating the virtual systems, and terminating the virtual systems;
    an MR data acquisition scanner;
    a control computer configured to communicate with the MR data acquisition scanner;
    wherein the virtual systems comprise a cloud-based virtual MR host with an active MR workflow, the cloud-based virtual MR host being connected on demand to the control computer; and
    at least one client processor configured to transmit patient-specific data to the cloud-based virtual MR host,
    wherein the cloud-based virtual MR host is configured to transmit the active MR workflow to the control computer in response to receiving the patient-specific data from the at least one client processor;
    wherein the control computer is configured to operate the MR data acquisition scanner to control an imaging procedure executed by the MR data acquisition scanner based on the active MR received from the cloud-based virtual MR host;
    wherein the at least one client processor is configured to evaluate image data received by the cloud-based virtual MR host; and
    wherein the active MR workflow includes MR parameter values for controlling the imaging procedure executed by the MR data acquisition scanner.

2. The MR imaging apparatus as claimed in claim 1, wherein the virtual systems each comprise a cloud-based virtual image reconstruction processor configured to receive raw data from the MR data acquisition scanner and to reconstruct image data from the raw data.

3. The MR imaging apparatus as claimed in claim 1, wherein each of the virtual systems comprises a cloud-based virtual host controller configured to control access by the at least one client processor to the cloud-based virtual MR host.

4. The MR imaging apparatus as claimed in claim 1, wherein the at least one client processor is configured according to at least one client type that includes at least one of a scan connection client, a post-processing client, a rendering client, and a referring client.

5. A method for implementing a magnetic resonance (MR) imaging procedure, comprising:
    transmitting patient-specific data from a client processor to a cloud-based virtual MR host;
    executing an active MR workflow in the cloud-based virtual MR host selected from a plurality of MR workflows in the cloud using the patient-specific data;
    connecting the cloud-based virtual MR host to an MR data acquisition scanner via a control computer connected to the MR data acquisition scanner;
    transmitting the active workflow from the cloud-based virtual MR host to the control computer in response to receiving the patient-specific data from the client processor;
    operating the MR data acquisition scanner via the control computer to control an imaging procedure executed by the MR data acquisition scanner based on the active workflow received from the cloud-based virtual MR host; and
    evaluating image data received from the cloud-based virtual MR host via the client processor.

6. A non-transitory, computer-readable data storage medium encoded with programming instructions, the storage medium being loaded into a control computer of a magnetic resonance (MR) imaging apparatus that includes an MR data acquisition scanner operated by the control computer, the programming instructions when executed by the control computer causing the control computer to:
    transmit patient-specific data from a client processor to a cloud-based virtual MR host;
    execute an active MR workflow in the cloud-based virtual MR host selected from a plurality of MR workflows in the cloud using the patient-specific data;
    connect the cloud-based virtual MR host to the MR data acquisition scanner via a control computer connected to the MR data acquisition scanner;
    transmit the active workflow from the cloud-based virtual MR host to the control computer in response to receiving the patient-specific data from the client processor;
    operate the MR data acquisition scanner via the control computer to control an imaging procedure executed by the MR data acquisition scanner based on the active workflow received from the cloud-based virtual MR host; and
    evaluate image data received from the cloud-based virtual MR host via the client processor.

7. The MR imaging apparatus as claimed in claim 1, wherein the active MR workflow further includes imaging process information for controlling the imaging procedure executed by the MR data acquisition scanner to acquire raw data for a patient who is associated with the patient-specific data.

8. The MR imaging apparatus as claimed in claim 7, wherein the active MR workflow further includes patient-specific information related to physical characteristics of the patient.

9. The MR imaging apparatus as claimed in claim 8, wherein the patient-specific information related to the physical characteristics of the patient includes at least one of patient height, patient weight, and tolerance to the use of a contrast agent.

10. The MR imaging apparatus as claimed in claim 1, wherein the action including at least one of generating the virtual systems, activating the virtual systems, deactivating the virtual systems, and terminating the virtual systems causes a data load of the MR imaging apparatus to be reduced.

11. The MR imaging apparatus as claimed in claim 7, wherein the control computer is configured to tailor the imaging procedure executed by the MR data acquisition scanner to the patient using the active MR workflow in accordance with the patient-specific data.

* * * * *